(12) United States Patent
Acker et al.

(10) Patent No.: US 8,034,113 B2
(45) Date of Patent: Oct. 11, 2011

(54) JOINT PROSTHESIS AND METHOD OF IMPLANTING SAME

(76) Inventors: Randall Lane Acker, Ketchum, ID (US); Gregory Thomas Van Der Meulen, Ketchum, ID (US)

( * ) Notice: Subject to any disclaimer, the term of this patent is extended or adjusted under 35 U.S.C. 154(b) by 983 days.

(21) Appl. No.: 11/237,171

(22) Filed: Sep. 27, 2005

(65) Prior Publication Data

US 2007/0073408 A1     Mar. 29, 2007

(51) Int. Cl.
*A61F 2/38* (2006.01)
(52) U.S. Cl. ............... 623/20.11; 623/20.12; 606/99
(58) Field of Classification Search .... 623/20.11–20.13, 623/23.4, 23.11, 23.12, 23.14, 23.15
See application file for complete search history.

(56) References Cited

U.S. PATENT DOCUMENTS

| | | | |
|---|---|---|---|
| 3,852,831 A * | 12/1974 | Dee ........................ | 623/20.11 |
| 4,293,963 A | 10/1981 | Gold et al. | |
| 4,301,552 A | 11/1981 | London | |
| 4,378,607 A * | 4/1983 | Wadsworth ............. | 623/20.11 |
| 4,538,306 A | 9/1985 | Dorre et al. | |
| 4,624,250 A | 11/1986 | Saunders et al. | |
| 4,822,364 A | 4/1989 | Inglis et al. | |
| 5,030,237 A | 7/1991 | Sorbie et al. | |
| 5,282,867 A | 2/1994 | Mikhail | |
| 5,376,121 A * | 12/1994 | Huene et al. ............ | 623/20.12 |
| 5,782,923 A | 7/1998 | Engelbrecht et al. | |
| 5,840,078 A | 11/1998 | Yerys | |
| 5,879,395 A | 3/1999 | Tornier et al. | |
| 6,051,751 A * | 4/2000 | Sioshansi et al. ............. | 128/898 |
| 6,132,468 A * | 10/2000 | Mansmann ................ | 623/20.16 |
| 6,162,253 A | 12/2000 | Conzemius et al. | |
| 6,168,626 B1 | 1/2001 | Hyon et al. | |
| 6,217,615 B1 * | 4/2001 | Sioshansi et al. .......... | 623/18.11 |
| 6,306,171 B1 | 10/2001 | Conzemius | |
| 6,409,768 B1 | 6/2002 | Tepic et al. | |
| 0,208,276 A1 | 11/2003 | Berelsman et al. | |
| 6,652,586 B2 * | 11/2003 | Hunter et al. ............. | 623/18.11 |
| 6,660,040 B2 * | 12/2003 | Chan et al. ................ | 623/22.21 |
| 0,186,581 A1 | 9/2004 | Huene | |
| 6,890,357 B2 | 5/2005 | Tornier | |
| 7,083,623 B2 | 8/2006 | Michelson | |
| 2003/0009171 A1 | 1/2003 | Tornier | |
| 2003/0220697 A1 | 11/2003 | Justin et al. | |
| 2004/0220675 A1 | 11/2004 | Lewis et al. | |
| 2004/0243243 A1 | 12/2004 | Tornier | |
| 2005/0165487 A1 | 7/2005 | Muhanna et al. | |

FOREIGN PATENT DOCUMENTS

DE    10061883    6/2002

(Continued)

OTHER PUBLICATIONS

VetLearn.com "Canine Elbow Dysplasia: Anatomy and Pathogenesis" C. Todd Trostel, DVM et al., vol. 25, No. 10, Oct. 2003.
The Knee Unicompartmental Knee Arthoplasty, Pagnanom, M. W. et al., 76, pp. 1002-1012, V. 1.

(Continued)

*Primary Examiner* — Bruce E Snow
*Assistant Examiner* — Melissa Hoban
(74) *Attorney, Agent, or Firm* — Klarquist Sparkman, LLP

(57) ABSTRACT

A novel and improved canine elbow prosthesis and method of implanting same including a unique bi-compartmental prosthesis having bone receiving members and transverse pegs which may be implanted with a minimally invasive surgical technique.

22 Claims, 11 Drawing Sheets

FOREIGN PATENT DOCUMENTS

| | | |
|---|---|---|
| EP | 0132284 | 1/1985 |
| EP | 1142542 | 10/2001 |
| EP | 1864617 | 12/2007 |
| GB | 2094638 | 9/1982 |
| GB | 2334890 | 9/1999 |
| WO | WO97/07753 | 3/1997 |

OTHER PUBLICATIONS

Non-final Office action dated Sep. 1, 2010, from related U.S. Appl. No. 12/011,337.

Final Office action, U.S. Appl. No. 12/011,337, filed Jan. 25, 2008, 20pp (Feb. 15, 2011).

* cited by examiner

JOINT PROSTHESIS AND METHOD OF IMPLANTING SAME

BACKGROUND

The article of manufacture and method relate broadly to a joint prosthesis and method of implanting same, and more particularly to a canine elbow prosthesis and novel and improved method of implanting same.

The elbow joint is a hinge-type synovial joint formed where the distal end of the humerus articulates with the proximal end of the radius and ulna. Elbow dysplasia is a common debilitating condition that affects many dogs. The current surgical techniques result in an unacceptable failure rate of the implant due to the technical difficulties associated with the implantation procedure as well as excessive post-surgical physical therapy needs as a result of the invasiveness of the procedure and the abundance of soft tissue damage.

There is therefore a need for a novel and improved joint arthroplasty that involves a minimally invasive surgical technique with a novel implant. The following embodiments and aspects thereof are described and illustrated in conjunction with systems, tools and methods which are meant to be exemplary and illustrative, not limiting in scope. In various embodiments, one or more of the above described problems have been reduced or eliminated, while further embodiments are directed to other improvements.

SUMMARY

The embodiments and methods set forth are exemplary and not for purposes of limitation. The present embodiments and methods are designed to provide a novel and improved elbow joint prosthesis and method of implanting same incorporating a first member having a first articulating surface portion of substantially hyperbolic paraboloid-shaped configuration as well as an opposite first bone fixation portion. A second member having a second articulating surface portion complementary to the first articulating surface portion, the second articulating surface portion having intersecting concave and convex surfaces defining alternate upwardly and downwardly curved projections as well as an opposite second bone fixation portion. The first and second members form an articulating prosthetic joint implant. The implant utilizes unique bone-stabilizing pegs as well as bone-receiving beads promoting bone ingrowth and reducing aseptic loosening. The anatomical duplication of the joint preserves flexion and extension while reducing excessive pulling of ligaments.

Methods are also provided for a novel and improved joint arthroplasty. One such method offered by way of example but not limitation, for implanting an elbow endoprosthesis comprises the steps of exposing a medial humeral condyle of a subject, drilling a hole through the medial condyle, removing a condylar crown of the condyle, resurfacing articulating surfaces of the joint, implanting the prosthesis and reattaching the condylar crown to the medial humeral condyle by applying pressure therebetween. The medial approach in elbow joint arthroplasty, which is usually the area most affected by elbow dysplasia is proposed. This will result in a lower failure rate of the implant due to superior biomechanics of the implant, a lower degree of invasion of the joint capsule and ligamentous structure while reducing periarticular scarring. Resurfacing arthroplasty results in less structural damage to the joint, provides good trabecular structure to support the implant without subsidence, low infection rates and little bleeding. The current implant may be inserted without disarticulating the joint thereby enabling an earlier return to weight bearing and walking while providing for a minimally invasive technique. The implantation of a bicompartmental prosthesis with only one implantation step is novel and reduces trauma to the subject.

The foregoing examples of the related art and limitations related therewith are intended to be illustrative and not exclusive. Other limitations of the related art will become apparent to those skilled in the art upon a reading of the Specification and study of the Drawings. In addition to the exemplary aspects and embodiments described above, further aspects and embodiments will become apparent by reference to the Drawings and by study of the following Description.

Exemplary embodiments are illustrated in referenced Figures of the drawings. It is intended by the embodiments and Figures disclosed herein are to be considered illustrative rather than limiting.

DESCRIPTION

Figure 6:
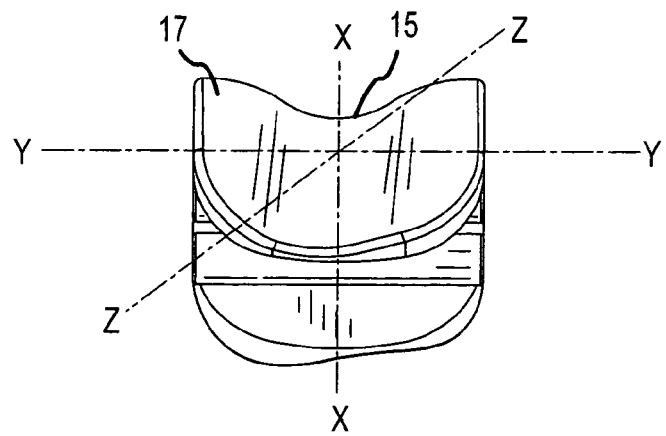
FIG. 6 is an elevational front view of the humeral component shown in FIG. 1.
Figures 3, 4, 5:
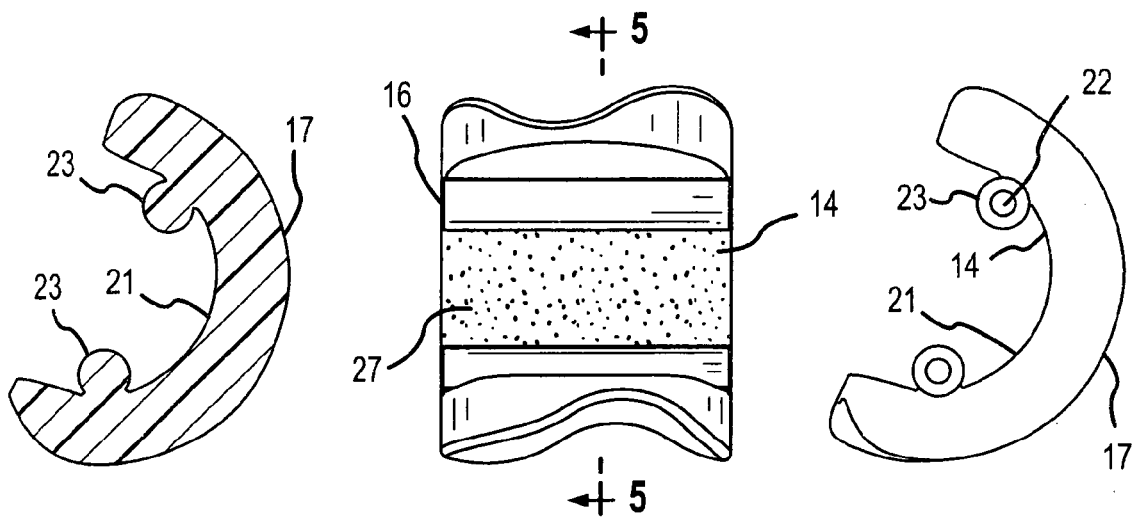
FIG. 3 is a top plan view of the humeral component as shown in FIG. 1.
FIG. 4 is a side view of the humeral component shown in FIG. 1.
FIG. 5 is a cross-sectional view about line 5-5 of the humeral component shown in FIG. 3.
Figure 7:
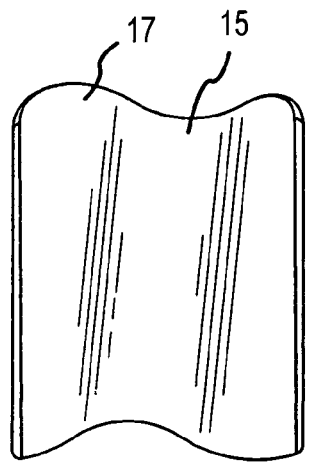
FIG. 7 is a bottom plan view of the humeral component of FIG. 1.
Figure 11:
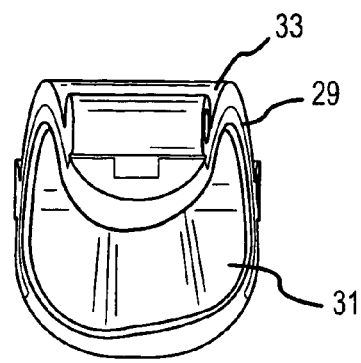
FIG. 11 is an elevational front view of the radioulnar component shown in FIG. 1.

In the embodiments shown in FIGS. 1 through 15, there is provided an implant 11 with a humeral condylar component 13 and a radioulnar component 29. The humeral component 13 includes a first articulating surface portion 17 of substantially saddle-shaped configuration, as shown in FIGS. 6 and 7, and an opposite first bone fixation portion 14, as shown in FIGS. 3 and 4. Geometrically, the saddle-shaped configuration of the first articulating surface portion 17 is broadly in the form of a hyperbolic paraboloid where sections parallel to and above the X-Y coordinates (horizontal plane) are hyperbolas symmetrical with the X axis, and sections parallel to and below the X-Y plane are hyperbolas symmetrical with the Y axis. Sections parallel to the other two coordinate planes are parabolas wherein those parallel to the X-Z plane open upward, while those parallel to the Y-Z plane open downward. See FIG. 6. The humeral condylar component 13 is made of cobalt-chrome (Co—Cr), molybdenum and titanium, Ti-alloy or ceramic but may also be made of other materials. The first articulating surface 17 as shown in FIG. 7 has a longitudinally extending angular groove 15 and simulates or approximates the natural shape of a canine trochlea humeri which is a medially located, pulley-shaped member on a canine. The groove 15 extends diagonally across the surface and extends at an acute angle to an imaginary line through a major axis of the first articulating surface portion 17.

The first bone fixation portion 14 of the humeral component 13 has a concave form 21 that is opposite to the first articulating surface 17 and includes transversely extending peg members or protuberances 23. The peg members 23 may be hollow or have shallow openings 22 at one end with the open end extending up to outer peripheral edges 16 of the first bone fixation portion 14. The openings 22 are designed to receive a retaining piece 47 which will be discussed in more detail at a later point. The pegs 23 typically are evenly spaced and extend transversely to a major axis of the humeral component 13. The peg members 23 may extend the width of the component 13 and in this embodiment do not extend beyond an outer peripheral edge 16 of the humeral component 13. Alternatively, the peg members 23 could extend beyond the outer edges of the component. The first bone fixation portion 14 may also include porous members, such as, PCA beads 27 which also promote bone growth. The PCA beads are manufactured by Bio-Vac, Inc of Michigan, USA. Other possible fixation members include hydroxyl apatite (HA) coating, titanium plasma spray coating or Resorbably Blast Media Coating to name a few. Bony fixation of prosthetic implants is encouraged with surface extensions, such as, the peg members 23 and beaded porous ingrowth surfaces. A proximal portion 20 of the humeral component 13 which is the first bone fixation portion 14 contacts a distal surface 28 of the humerus 12 providing for an interference fit between the bone fixation portion and the humerus 12. See FIG. 2.

Figures 8, 9, 10:
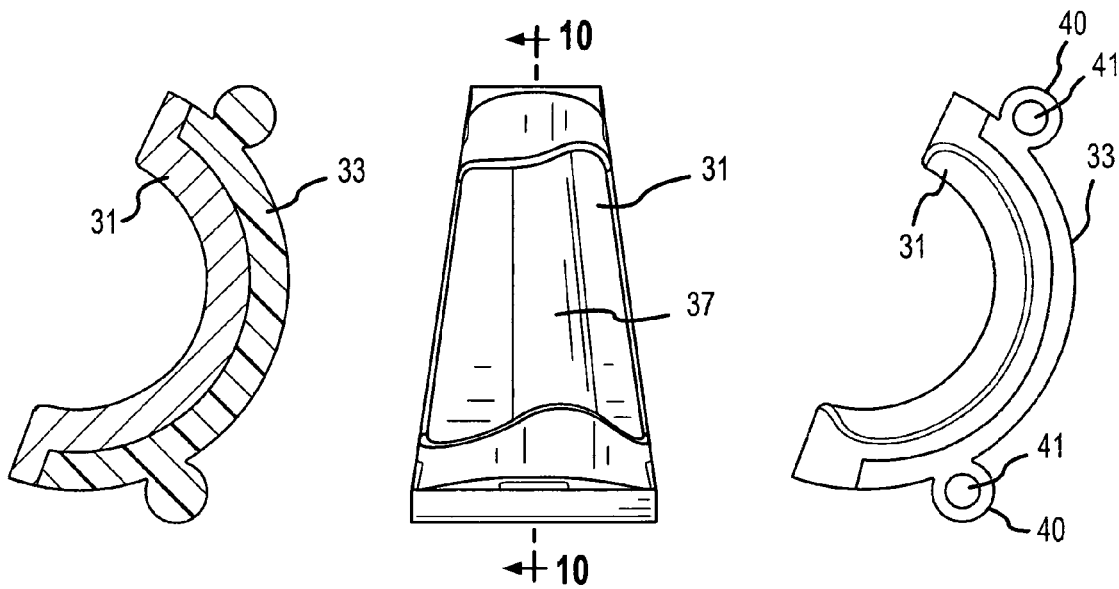
FIG. 8 is a top plan view of the radioulnar component shown in FIG. 1.
FIG. 9 is a side view of the radioulnar component shown in FIG. 1.
FIG. 10 is a cross-sectional view taken about line 10-10 of the radioulnar component shown in FIG. 8.

The radioulnar component 29 has opposing surfaces including a second articulating surface portion 31 and a second bone fixation portion 33. The radioulnar component 29 is half-moon shaped and is slightly tapered at a posterior end. The second articulating surface portion 31 has a saddle-shaped configuration that faces cranially. The articulating surface portion 31 contains a medial ridge member 37 having intersecting convex and concave surfaces defining alternate upwardly and downwardly curved projections. The ridge member 37 simulates a canine trochlear notch and is complementary to the groove 15 of the first articulating surface portion of the humeral component 13. The ridge 37 as shown in FIG. 8, extends diagonally across the concave surface at a mid-level portion between the concave and convex surfaces and extends at an acute angle to an imaginary line through a major axis of the second articulating surface portion 31. The angular extension of the ridge 37 approximates the natural angular extension of a trochlear notch.

Figure 1:
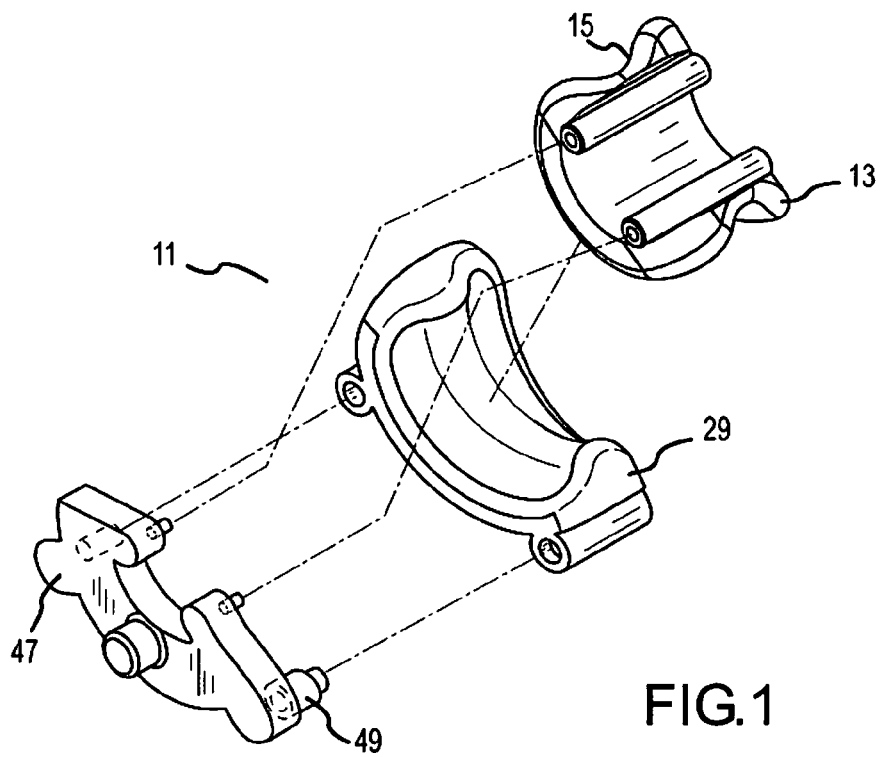
FIG. 1 is an exploded view in perspective of an embodiment of a joint prosthesis.

As shown in FIG. 1, the first articulating surface portion 17 of the humeral component 13 forms an articulating system with the second articulating surface portion of the radioulnar component 29. The radioulnar component 29 as shown in FIGS. 9 and 10 is made of two pieces, namely, the second articulating surface portion 31 which is made of ultra-high molecular weight polyethylene but may also be made of other materials and the second bone fixation portion 33 which is composed of cast cobalt chrome molybdenum, titanium or ceramic, as well as other materials. This allows the articulating surfaces of the humeral and radioulnar components 17 and 31 to have metal-on-plastic contact. Other combinations may be used without departing from the intent of providing a smooth, articulating surface.

Figure 12:
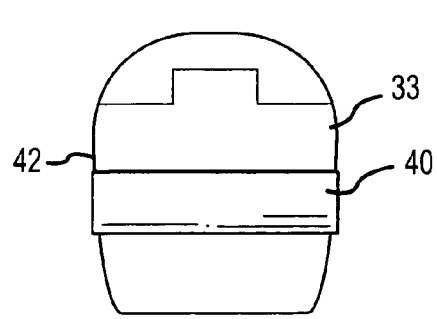
FIG. 12 is a rear view of the radioulnar component shown in FIG. 1.
Figure 13:
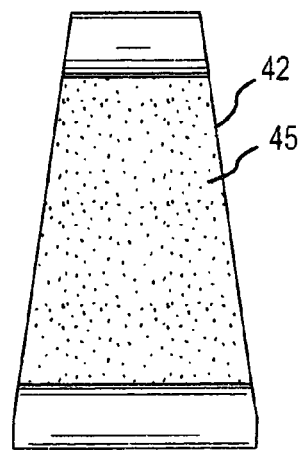
FIG. 13 is a bottom plan view of the radioulnar component shown in FIG. 8.

The second bone fixation portion 33 of the radioulnar member 29 contains at least one porous peg member 40 with a hollow opening 41 to aid in implant positioning and bone reabsorption. As with the transversely extending peg members 23 of the humeral component 13, the porous peg members 40 of the radioulnar component 29 also may be transversely extending along a major axis of the radioulnar component 29. Further, the porous peg members 40 in this embodiment as shown in FIG. 12 do not extend beyond the outer peripheral edge 42 of the second articulating surface portion 31 of the radioulnar component 29. This is by way of example, but the porous peg members may also extend beyond the outer peripheral edges of the radioulnar component. As with the humeral component 13, the second bone fixation portion 33 of the radioulnar component 29 may also integrate porous beads 45 to promote bone ingrowth. A distal portion of the radioulnar component 29 which is the second bone fixation portion 33 contacts proximal surfaces of the ulna 51 and radius 53 providing for an interference fit between the second bone fixation portion 33 and the radius and ulna.

In one embodiment, the groove 15 and ridge member 37 are not centered but the complementary components are longitudinally extending and intersect a major axis only at the center as discussed previously, requiring a different joint prosthesis for the right and left joints. It will be evident that in another embodiment, the prosthesis including humeral and radioulnar components, which is isometric, can be used for a right or left joint arthroplasty with the complementary components extending longitudinally along a centered vertical plane.

Figure 2:
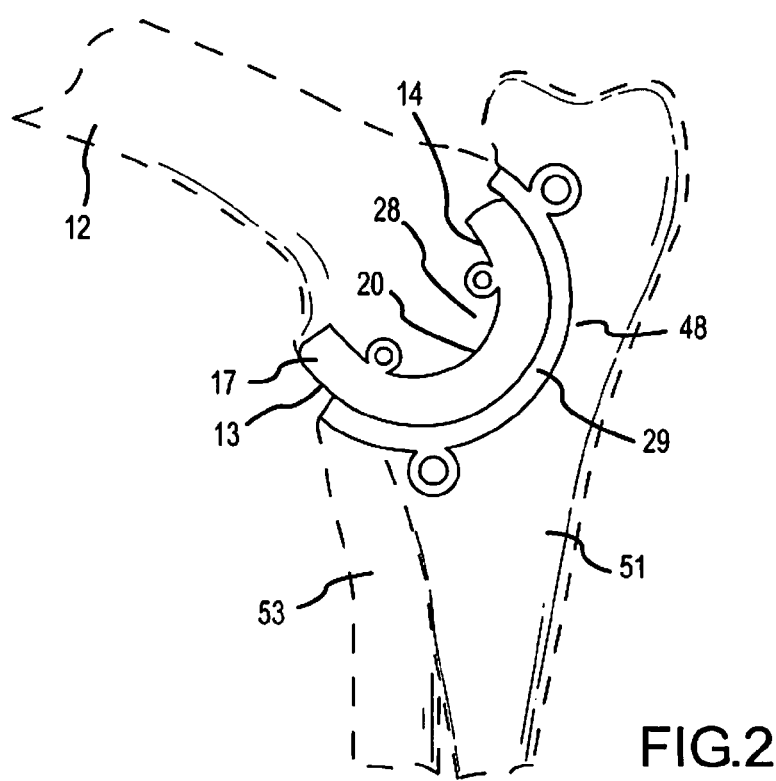
FIG. 2 is a side view of the implant of FIG. 1 including the canine humerus, radius and ulna.
Figure 14:
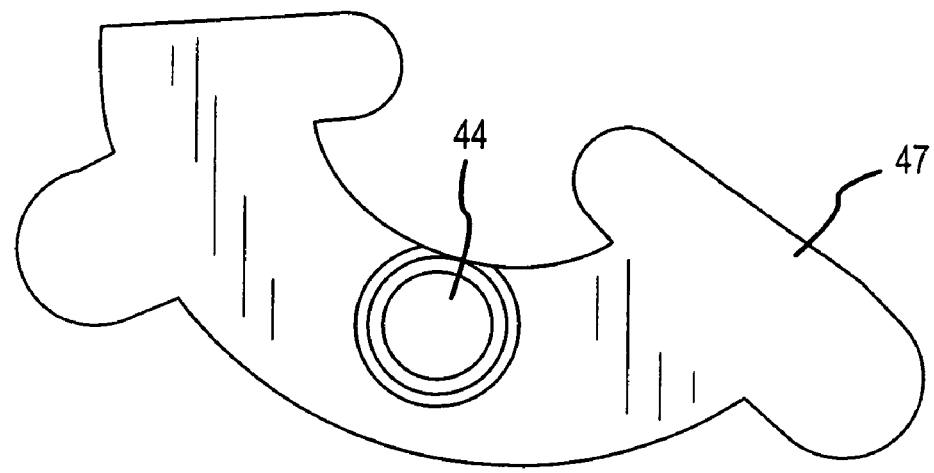
FIG. 14 is a top plan view of the retaining element shown in FIG. 1.
Figure 15:
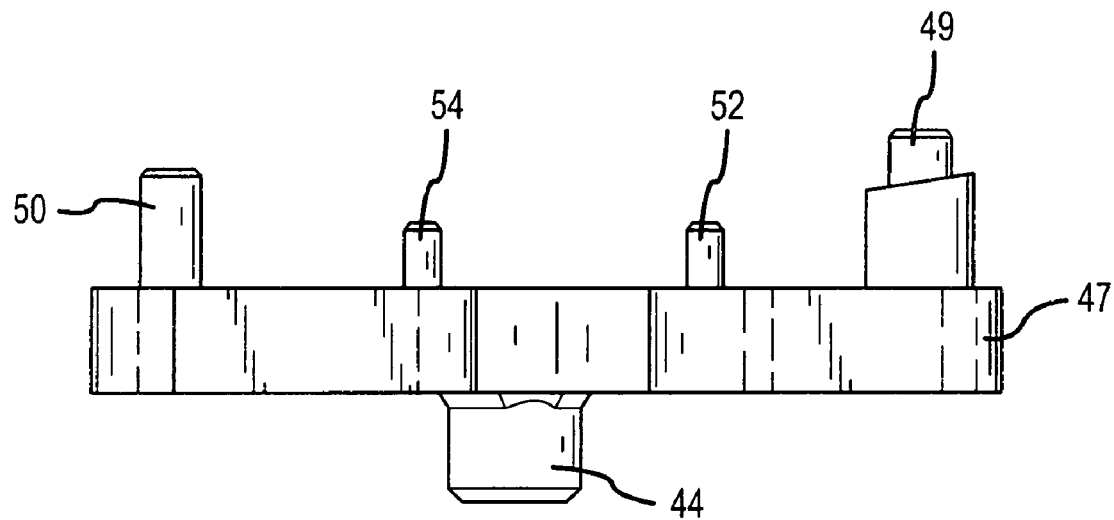
FIG. 15 is a side view of the retaining element shown in FIG. 1.

The articulating surfaces of the humeral and radioulnar components are polished to a smooth finish promoting unencumbered articulation between the two surfaces. The bone fixation portions of the humeral and radioulnar components contain the porous peg members 23 and 40 as well as the porous beading 27, 45 on their surfaces to promote bone ingrowth. The humeral and radioulnar components 13 and 29, respectively, are releasably linked together with an aligning or retaining piece or retainer 47 as shown in FIGS. 1, 14 and 15 which aids in positioning of the implant 11 within the joint cavity 48 as shown in FIG. 2 and is removed once the implant is securely in place. The implant retainer 47 serves multiple functions. Due to the complex articular surfaces of the humeral and radioulnar components, it is necessary that when placed in the subject, both components be oriented at the proper depth and in the correct state of articulation. The canine elbow is typically aligned at 90° flexion. The implants, to function correctly together, should both be at their respective 90° of flexion. The retaining piece 47 has four posts 49, 50, 52 and 54 that releasably link the humeral component 13 and the radioulnar component 29. See FIG. 1. The posterior ulnar post 49 on the retainer 47 is slightly larger and is slightly angled which compensates for the tapering in the posterior end of the radioulnar component 29 and assures that the implants cannot go in crooked or at an angle to the sagittal plane that exists at the elbow at the point of intersection between the center line of the humerus and the center line of the radioulnar component. The retainer 47 also functions as a tool in which one can press or hammer upon an extension 44 of the retainer 47 to assure maximum insertion into the joint cavity of the implant 11. Due to the nature of the implant, the radioulnar component 29 relies heavily upon the press-fit nature of the component to insure stability. The humeral component 13 is captured between the medial and lateral epicondyles preventing movement laterally on a frontal or transverse plane.

Figure 20:
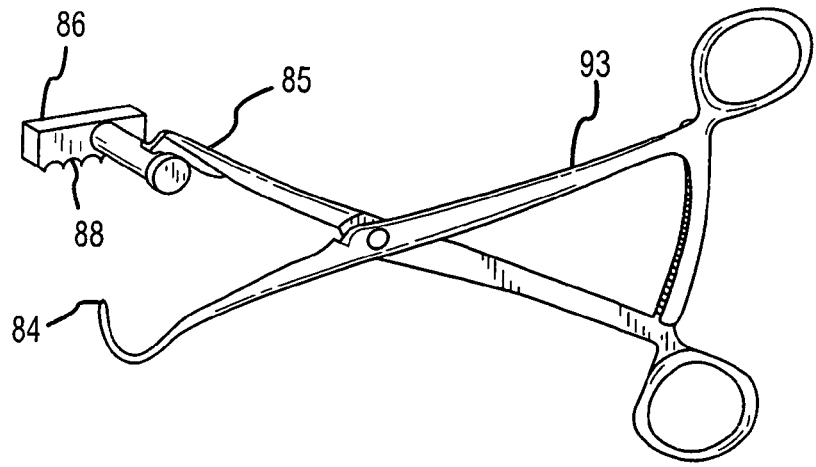
FIG. 20 is a perspective view of a medial epicondylar osteotomy guide.
Figure 21:
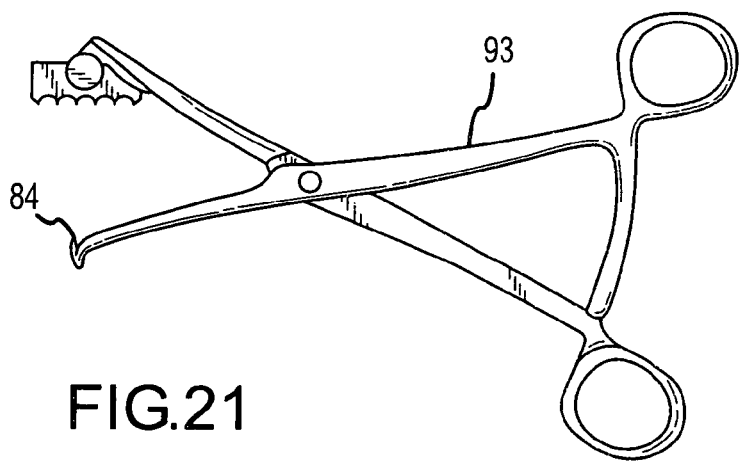
FIG. 21 is a top plan view of the medial epicondylar osteotomy guide shown in FIG. 20.
Figure 22:
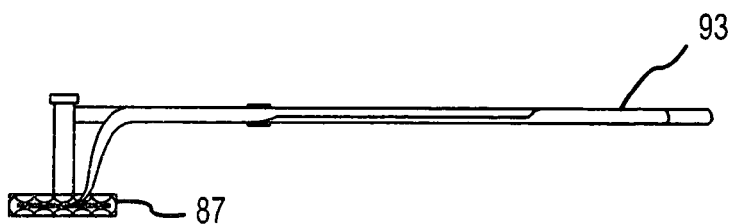
FIG. 22 is a side view of the medial epicondylar osteotomy guide shown in FIG. 20.

As embodied and broadly described herein, the elbow arthroplasty of the present embodiment includes a humeral component 13 and a complementary radioulnar component 29 as well as the retaining piece 47. There will also be described a novel and improved method for implantation as well as embodiments of a positioning device 55 as shown in FIGS. 16-19 with an angular support arm 66 and a drill guide 81; an osteotomy guide 93 as shown in FIGS. 20-22 and an alignment and drill guide 103 and 105, respectively, as shown in FIGS. 23-26 for the installation of the implants. Broadly, the positioning device 55 immobilizes and positions a joint for prosthesis implantation. The positioning device 55 is adjustable so that different size joints may be positioned. The positioning device 55 in combination with the drill guide 81 allows for accurate drilling on a joint while the positioning device in combination with a burr and a base 59 allow for accurate removal of cartilage and minimal subcondylar bone from a joint.

The implant 11, instruments and method are useful in the treatment of degenerative joint disease in canines as well as other species including humans and allow for a minimally invasive implantation technique. The joint capsule is not disarticulated during the process and the ligaments and muscles remain attached to the condylar crown. The bicompartmental prosthesis is implanted in one stage as opposed to separate stages which involve securing the implant in consecutive steps to the humerus, radius and ulna.

In one method, a radiographic evaluation including X-rays as well as arthroscopic surgery are performed on the subject to determine the degree of disease and to measure and estimate the proper size of implant to be used in the procedure. A Mylar overlay, not shown, is also used to determine the size of the implant necessary. The ulna 51 and the radius 53 are fused to allow fixation of the radioulnar component to the radius and ulna.

Figure 16:
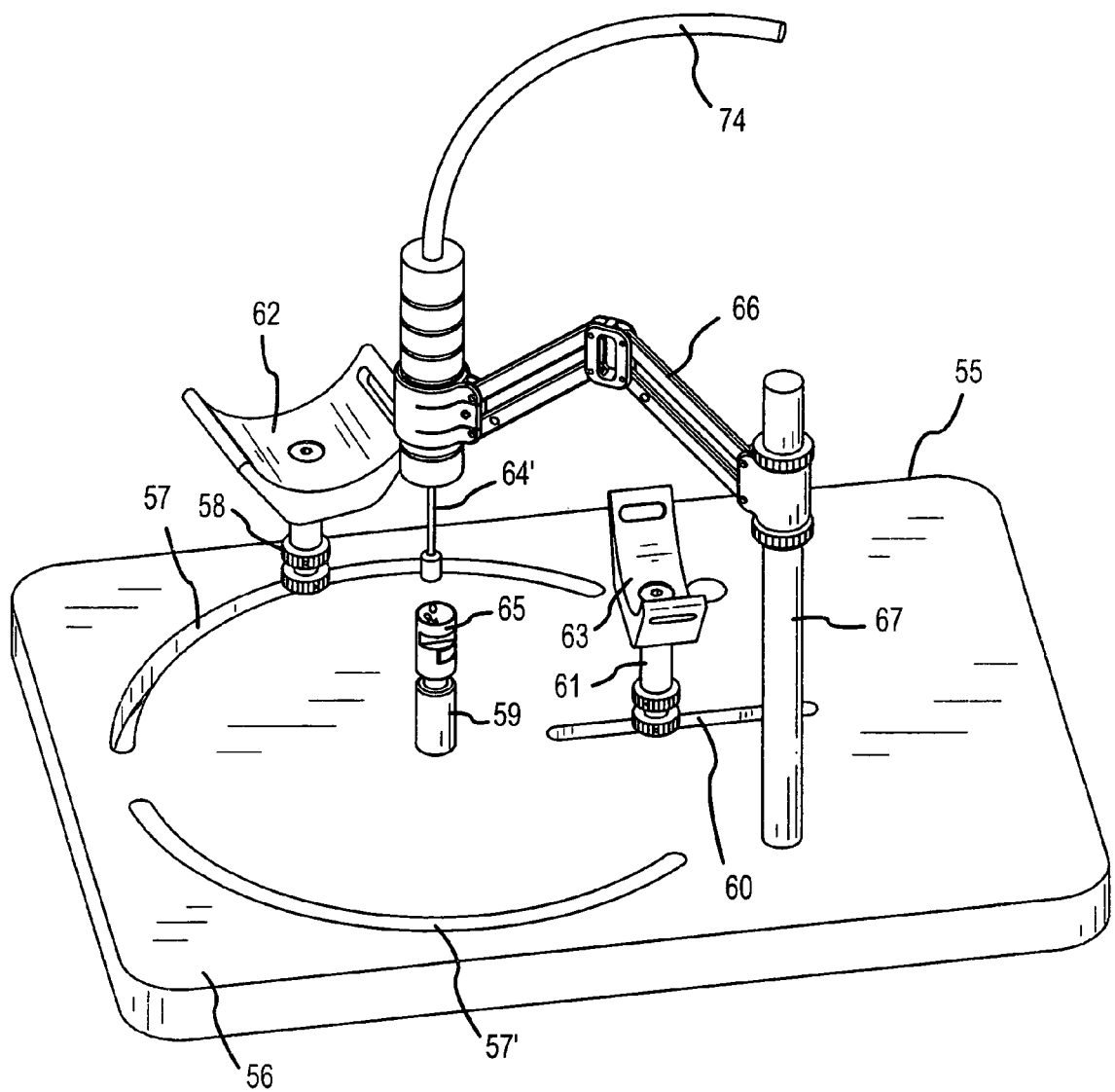
FIG. 16 is a perspective view of a positioning system.

The subject is then stabilized with the positioning device 55 as shown in FIGS. 16 and 20. The positioning device consists of a tray or base 56 having numerous apertures which in one embodiment includes opposing spaced arcuate slots 57, 57' for insertion of a lower cylindrical end 58' of an adjustable post member 58. A lock nut 58" is threadedly adjustable to establish the desired effective height of the post 58, and the post 58 is both slidable and rotatable with respect to the tray 56. The tray 56 also includes a linear slot 60, also adapted to receive a post member 61 that is adjustable in the same manner as the post 58. The arc section post 58 supports an upwardly facing, saddle-shaped radioulnar cradle 62 with a clamp or strap 69 and the linear section post 61 supports an upwardly facing, saddle-shaped humeral cradle 63 with a clamp or strap 69'. The tray 56 includes the base 59 that is designed to support and immobilize the epicondyle of a subject. The arc-shaped slots 57, 57', linear slot 60 in combination with the post members 58, 61 and the base 59 allow for a subject joint to be taken through 120° of rotation without having to reposition the patient. This will be discussed at a later stage. Further, the opposing arc sections 57, 57' allow for immobilization and rotation of the reverse joint from a medial or lateral aspect. For example, the positioning system 55 with the opposing arc-shaped slots 57, 57' allow for immobilization of a subject's left or right joint, also allowing for approach from a medial or lateral aspect. The linear section post 61 is both slidable and rotatable to accommodate a variety of appendage sizes.

The positioning device 55 also includes a support post 67 over which one end of an adjustable arm 66 fits. The arm 66 includes a universal swivel 66' at its center and opposite ends so as to be capable of twisting as well as moving vertically and horizontally. A free end of the arm 66 includes a clamp 83 that enables attachment of a resurfacing component such as a drill or handpiece 72. In this instance the handpiece is manufactured by Blackstone Industries, Inc. of Bethel, Conn. enabling a user to attach, for example, a burr or drill. The handpiece may take many forms and is not limited to the device shown but is designed to allow attachment of a tool for accomplishing a multitude of tasks such as, the accurate removal of bone and cartilage. The handpiece 72 has a flexible shaft 74 running to an electric motor, not shown. The handpiece 72 is clamped to the adjustable arm 66 with clamp 83 and enables the user to accurately remove cartilage and bone from a vertical or horizontal position, virtually removing operator error. The swivel arm may take many forms but is designed to enable an approach from virtually any angle while providing stabilization. The adjustable arm 66 as well may take different forms and may be positioned at various angles once again to allow for varied approaches in stabilization. The arm 66 may hold a multitude of tools including lasers, light sources and scalpels to name a few.

Figure 17:
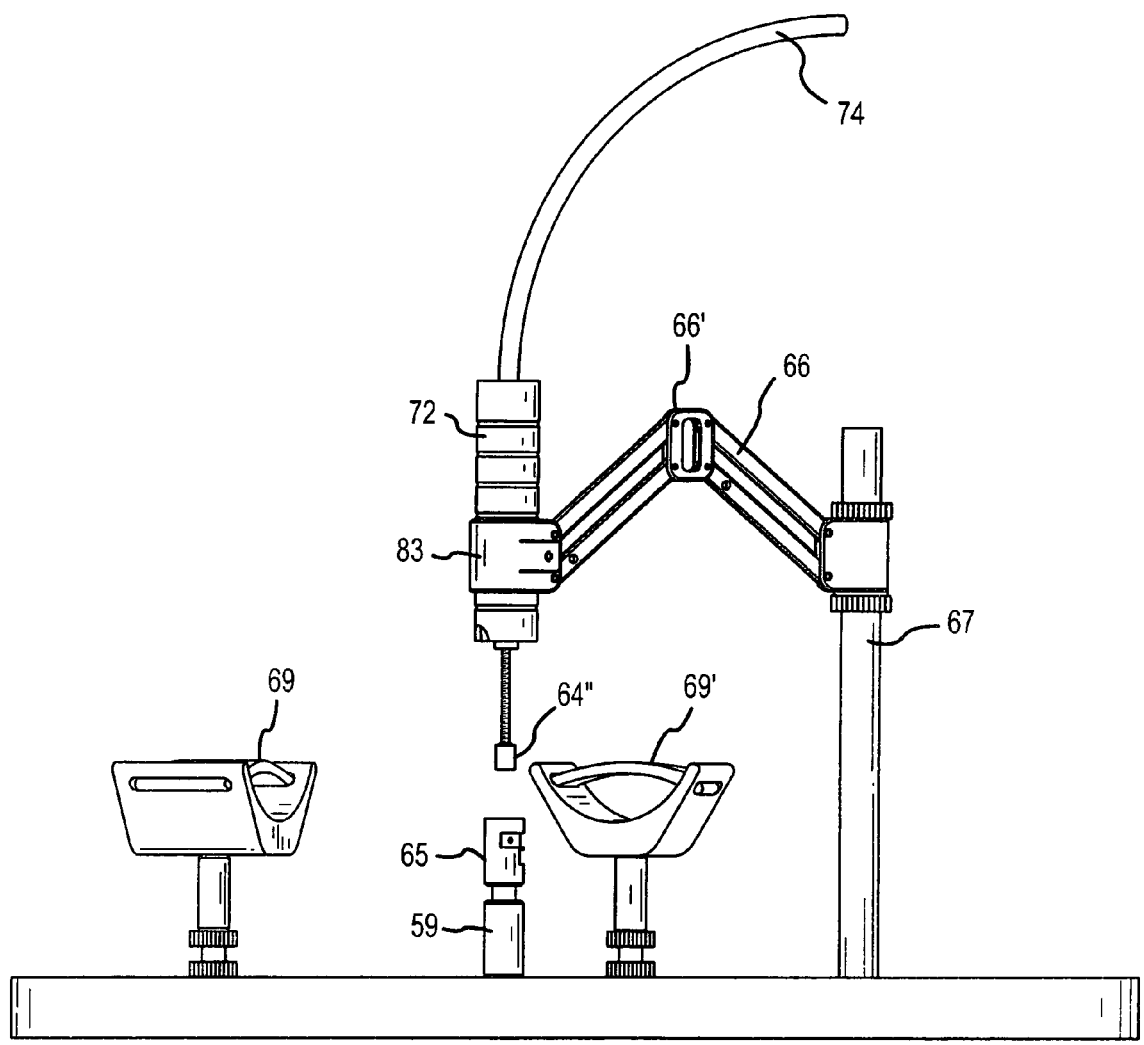
FIG. 17 is a side view of the positioning system shown in FIG. 16.
Figure 18:
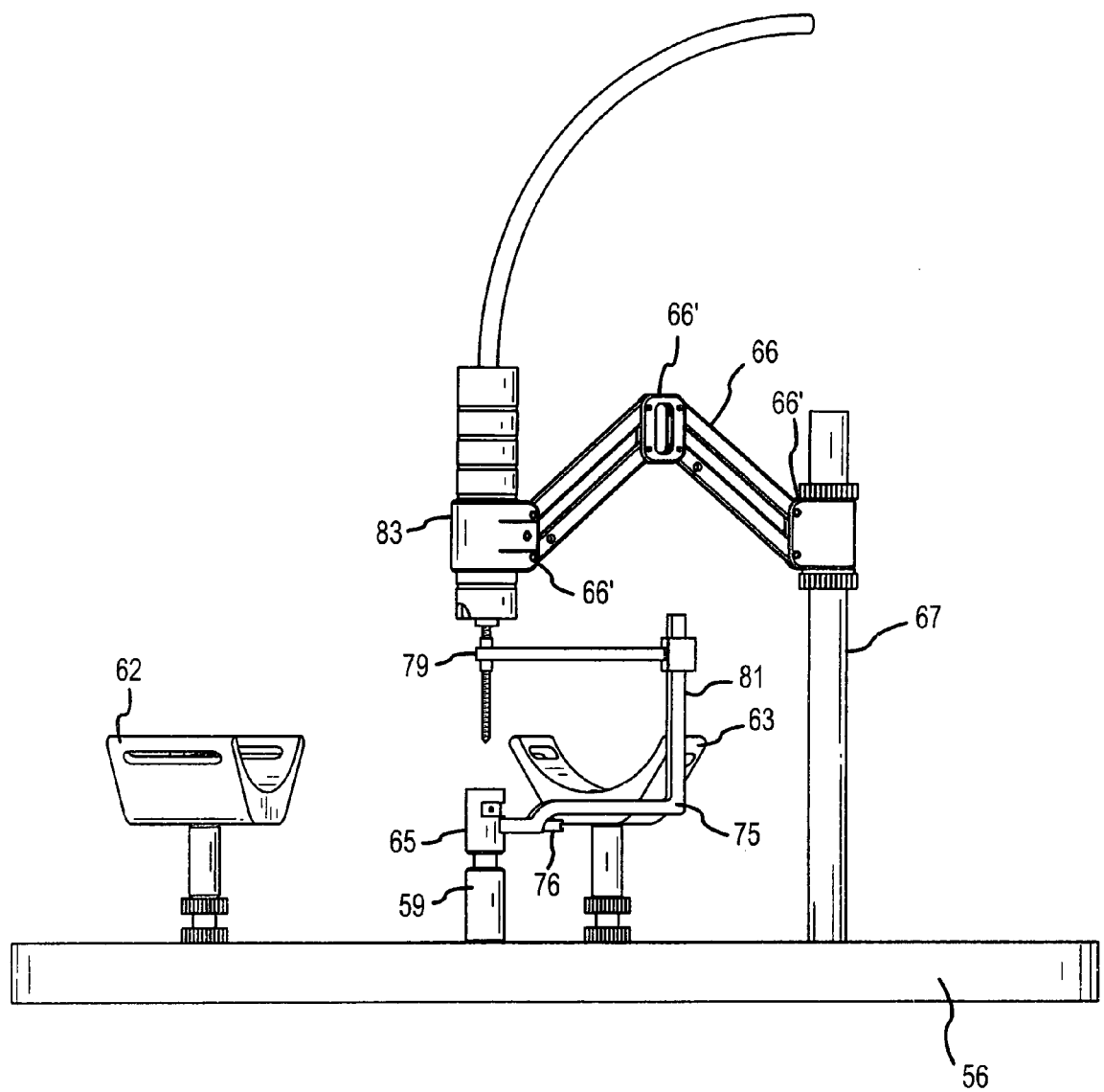
FIG. 18 is a side view of a positioning system.
Figure 19:
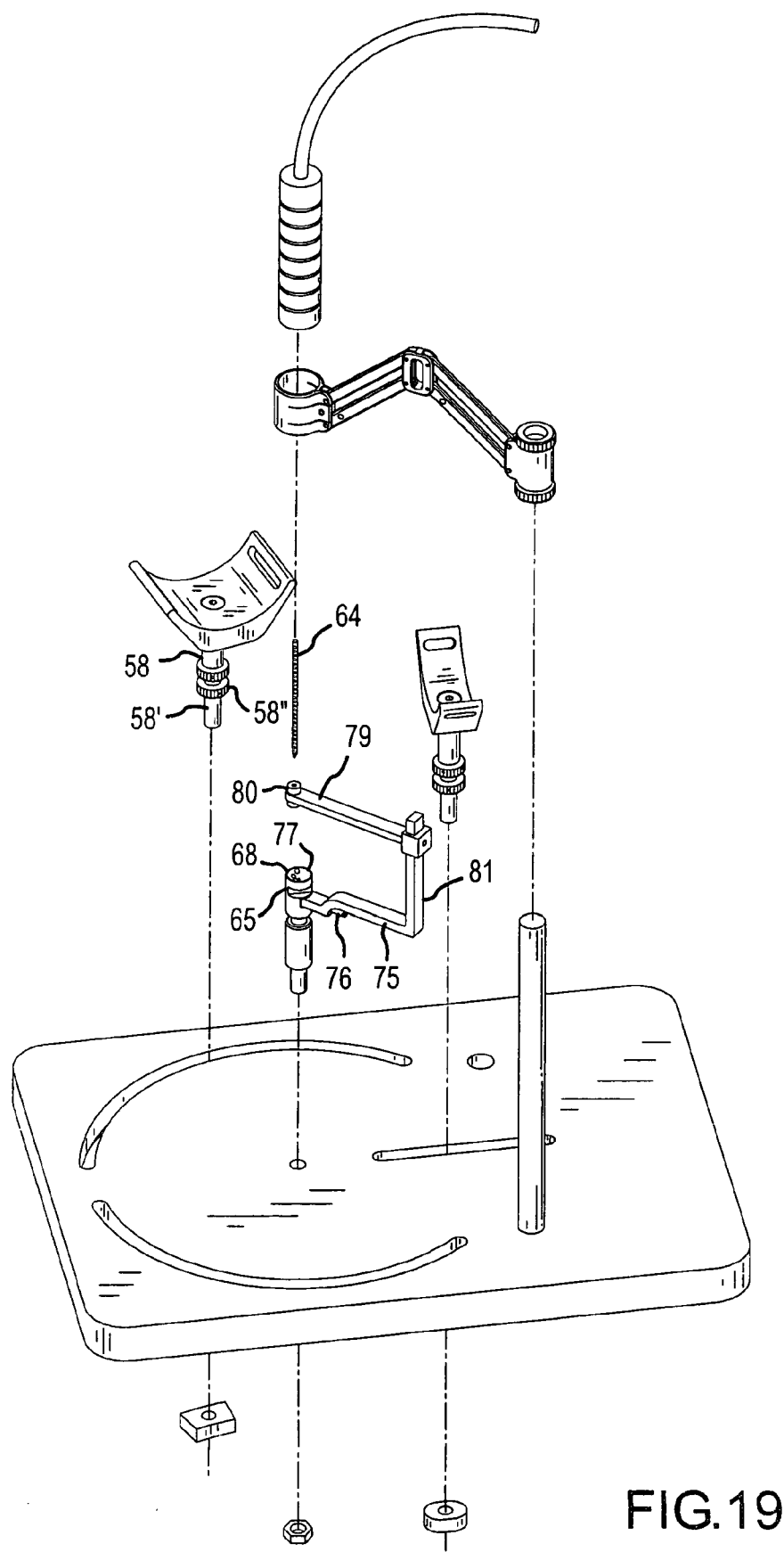
FIG. 19 is an exploded diagrammatic view of the positioning system shown in FIG. 18.

It will be evident that the positioning device 55 is also conformable for use with the drill guide 81 as shown in FIGS. 18-19. The drill guide 81 has an arm 75 extending horizontally and upwardly as shown in FIG. 18. The drill guide 81 attaches to the base 59 at a variety of possible locations, shown in FIGS. 16-19 at 65, depending upon the size of the joint and location of the center of rotation on the particular subject. The base 59 has an upper flat surface 77 including 3, 2.5 mm holes 68 that are 2 mm to 6 mm off-center, in 2 mm intervals, approximately 45° cranial and distal, depending upon the elbow, that allows for a 2.5 mm drill 64 to pass through. A 2.5 mm center of rotation (COR) post 70 as shown in FIGS. 23 and 25 is inserted through the drilled opening in the joint to aid in positioning of the joint during the drilling and burring process.

Attached to the drill guide 81 is a drill guide arm 79 which lines up with one of three holes 68 located on the surface 77 of the base 59. A thumbscrew 76 attaches the vertical arm 75 to the base 59. The drill guide arm 79 possesses a drill guide hole 80 through which the 2.5 mm drill bit will fit. This aids in drilling off-center holes for optimizing the location of the center of rotation of the elbow. See FIG. 19. The drill guide 81 is typically used in conjunction with the positioning system 55 for accurate drilling purposes.

As an example, the humerus 12 of a canine is placed in the humeral cradle 63 and secured, the fused radius 53 and ulna 51 of the canine is secured in the radioulnar cradle 62 and secured, exposing the canine's medial joint for osteotomy. The joint is placed on the base 59 and is stabilized. As referred to earlier, a 2.5 mm hole, "COR hole" is drilled through the epicondyle, medial to lateral, using the drill guide arm 75 and passing a 2.5 mm drill 64 through the drill guide hole 80, the epicondyle and the corresponding hole 68 in the base 59. The COR hole aids in proper positioning of the implant as well as positioning of the alignment and drill guides. Once the COR hole is drilled, the osteotomy guide 93 as shown in FIGS. 20-22 is clamped to the medial epicondyle of the subject. The osteotomy guide 93 is a hemostat-like instrument having a first end 84 that establishes a contact point with the joint, typically along the articular cartilage on the cranial side of the humerus. A second end 85 having an osteotomy plate 86 including a cutting groove 87 that lies along the same horizontal plane as the contact point 84 and a serrated portion 88 which clamps onto the epicondyle. A saw blade, not shown, is inserted through the cutting groove 87 and intersects with the contact point 84 that has been secured to the caudal ridge of the distal end of the humerus. The guide allows for accurate bone cutting without removing excessive bone which tends to result in subsidence. The osteotomy guide also minimizes invasion of the joint capsule. Once the medial epicondyle has been osteotomized, not shown, the cut portion which is the condylar crown is reflected back along with the attached muscles and ligaments, exposing the distal medial humeral condyle.

Figure 23:
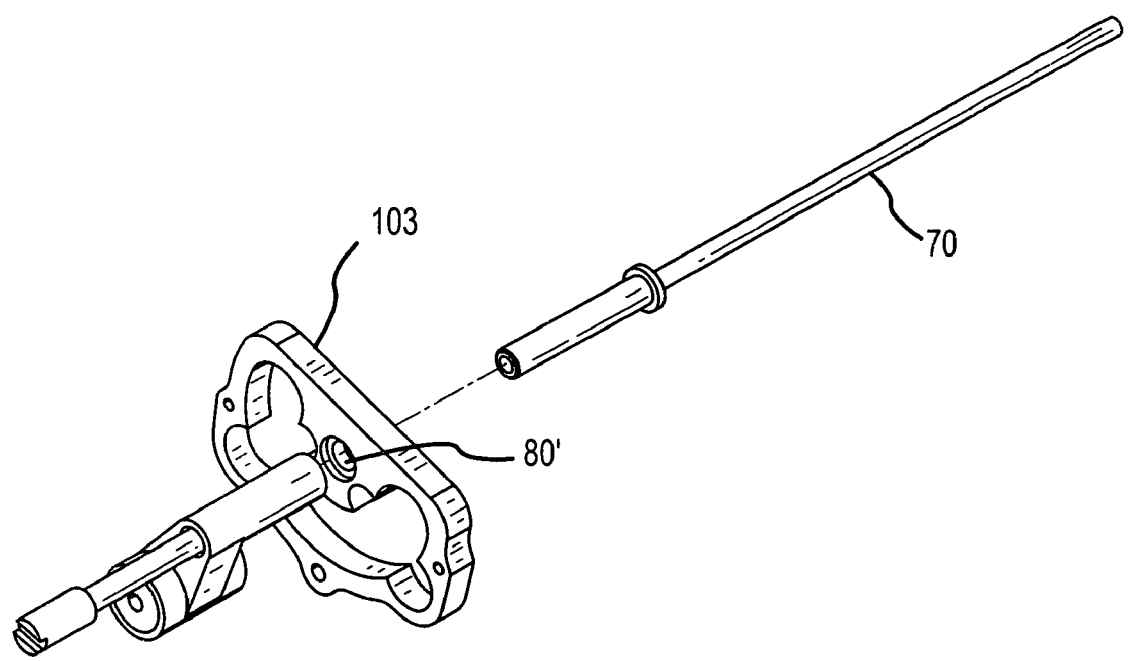
FIG. 23 is a perspective view of an alignment guide and Center of Rotation post.
Figure 24:
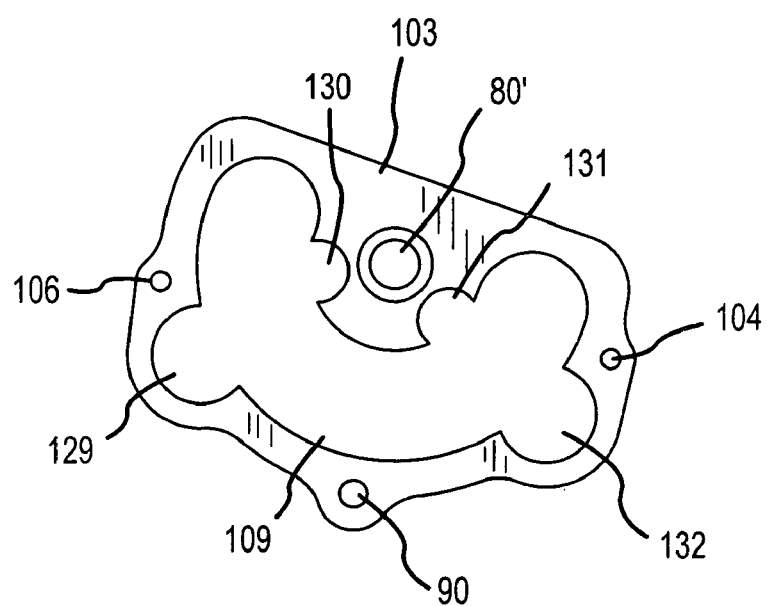
FIG. 24 is a top plan view of the alignment guide shown in FIG. 23.
Figure 25:
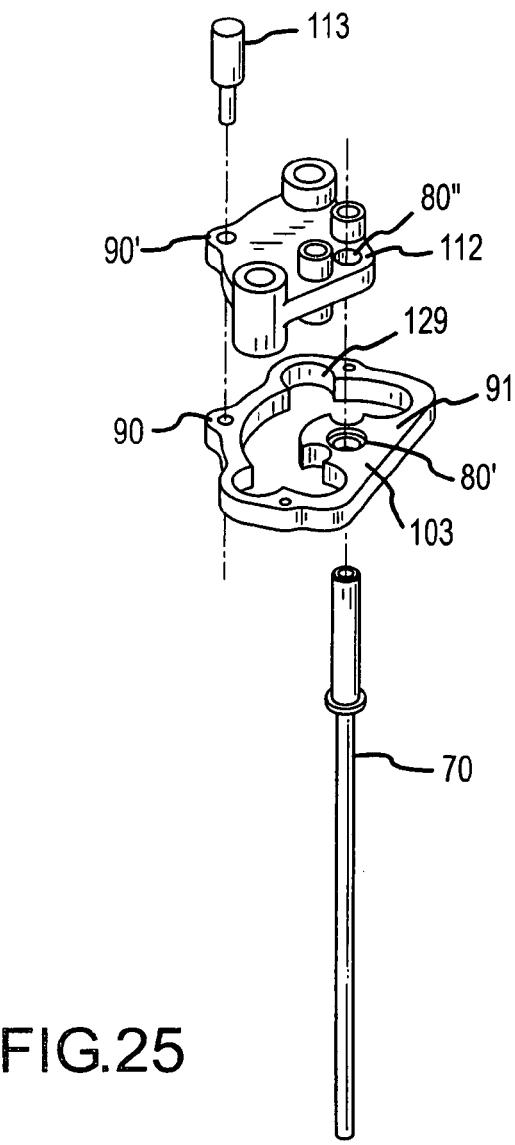
FIG. 25 is an exploded view of the alignment guide and a drill guide.
Figure 26:
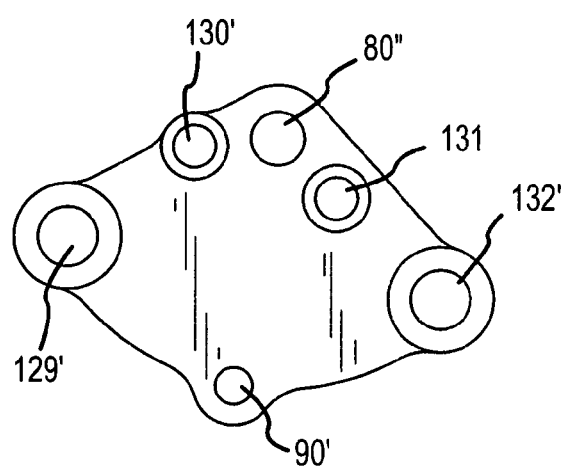
FIG. 26 is a top plan view of the drill guide shown in FIG. 25.

The next step involves attaching the alignment guide 103 as shown in FIGS. 23 to 25 with the COR post 70 to the positioning system 55. The 2.5 mm hole which was previously drilled accommodates the COR post 70 through the epicondyle. The COR post 70 is inserted through the 2.5 mm hole, into the base 59 and the alignment guide 103 is attached by sliding the alignment guide 103 over the COR post 70 at point 80' as shown in FIG. 23. The guide 103 is rotated until cranial peg hole 129 lines up with the cranial proximal ulnar and the caudal portion of the radius. K-wires are inserted down through respective holes 104 and 106 in the alignment guide and into the joint, locking the guide in the desired position. The alignment guide 103 is in the same shape as a cross-section of the entire implant at a 90° articulation.

A specially designed burr saw 64' shown in FIGS. 16 and 17 is inserted into the handpiece 72. The handpiece is clamped to the arm 66 with clamp 83. The burr saw 64' is designed with a slightly larger head 64" which acts as an "end mill" or "router bit" to accurately remove remaining cartilage and minimal subcondylar bone while preserving good trabecular structure. Subsidence typically occurs when the compressive stresses or trabecular bone struts exceed the strength of the bone, resulting in microfractures and resorption of trabeculae. Resurfacing of the trochlea humeri and the trochlear notch of the radius and ulna is performed with the burr saw 64' and a depth measuring device or depth limiting stop, not shown, is used to insure proper depth penetration. The burr saw removes the large arc-shaped portion 109 within the alignment guide 103, leaving four smaller areas consisting of the openings 129, 130, 131, 132 that accommodate the peg members 23 and 40 of the implant 11 for the drill 64 to remove.

Due to the insertion of the implant from the medial aspect, the humeral and radioulnar articulating surfaces may be resurfaced without having to break or otherwise open or expose the articulating surfaces of the elbow joint. The removal of articular cartilage as well as a minimal amount of subcondylar bone on both sides of the joint simultaneously without having to disarticulate the joint allows for a minimally invasive procedure.

Once the alignment guide 103 has been inserted and the majority of resurfacing is complete, a drill guide plate 112 is placed on a top surface 91 of the implant alignment guide 103. It slides down over the COR post 70 at point 80" and has four holes 129', 130', 131', 132' that line up with the holes 129, 130, 131, 132 on the alignment guide. It is then locked in place by a screw 113 passing through the drill guide 112 and into the alignment guide 103 at points 90, 90'. Using the angular support arm 66 and the handpiece 72, a specified drill size is chosen and inserted into the handpiece 72. The drill bit 64 is lined up with the opening 80 in the arm guide 75 and four holes are drilled corresponding with the holes 129', 130', 131', 132' on the drill guide plate 112. The drill guide plate 112 is then removed.

The implant 11 is lined up with the implant retaining plate 47 in place, all four holes lining up with the four horizontal pegs 23, 40 located on the first bone fixation portion 14 of the humeral component 13 and the second bone fixation portion 33 of the radioulnar component 29. This allows the implant 11 to be inserted where the cancellous articulating surfaces have been removed. Using a hammer device, not shown, the implant 11 will be tapped into place within the elbow joint. With the pegs running horizontally, the implant may not rotate on a sagittal plane while inside the elbow. The horizontal pegs also prevent the implant from sliding side to side based on a press-fit of the joint.

The implant is set on the distal medial humeral condyle and is impacted or pounded so that there is almost no distance between the implant and the bone. Optimally, the implant is set within 1 mm of the bone. If there is more than 1 mm. of space between the implant 11 and the bone, there is typically poor bone ingrowth. Cementless fixation is utilized in our method but is set forth as an example, not as a limitation. Once the implant is in place, the medial epicondylar crown, including the attached ligaments and muscles, is reattached, not shown, using a 3.5 mm cancellous screw and a spiked washer, both not shown. The cancellous screw is manufactured by Veterinary Orthopedic Implant or Synthes and New Generation Devices. The spiked washers are also manufactured by Veterinary Orthopedic Implants and Synthes.

While a number of exemplary aspects, embodiments and methods have been discussed above, those of skill in the art will recognize certain modifications, permutations, additions and subcombinations thereof. It is therefore intended that the following appended claims and claims hereafter introduced are interpreted to include all such modifications, permutations, additions and subcombinations as are within their true spirit and scope.

We claim:

1. A joint prosthesis comprising:
   a first implant member having a first front articulating surface portion of substantially hyperbolic paraboloid configuration and a first rear concave bone fixation surface portion to be fitted to an end of a first bone;
   a second implant member having a second front articulating surface portion including mutually perpendicular intersecting concave and convex surfaces defining alternate upwardly and downwardly curved projections complementary to and engageable with said first front articulating surface portion and including a second rear convex bone fixation surface portion to be fitted to an end of a second bone that articulates with the first bone; and a retaining member configured to releasably link together the first and second implant members and prevent movement therebetween, wherein said first and second bone fixation surface portions each include two or more porous protuberant members extending transversely to said bone fixation surface portions, and wherein the retaining member comprises at least a first and second post positioned to be at least partially inserted into the porous protuberant members on the first bone fixation surface portion and at least a third and fourth post positioned to be at least partially inserted into the porous protuberant members on the second bone fixation surface portion, the posts and protuberant members having parallel longitudinal axes to allow each post to be inserted into its respective protuberant member to link together the first and second implant members and, after implantation, allow each post to be slidably withdrawn from its respective protuberant member to allow the first and second implant members to articulate.

2. A joint prosthesis according to claim 1 wherein a ridge member on said second articulating surface portion extends diagonally across said concave surface at a mid-level portion between said convex and concave surfaces.

3. A joint prosthesis according to claim 2 wherein said ridge member extends at an acute angle to an imaginary line through a major axis of said second articulating surface portion.

4. A joint prosthesis according to claim 2 wherein a medial groove on said first articulating surface portion is complementary to said ridge member on said second articulating surface portion.

5. A joint prosthesis according to claim 1 wherein said second articulating surface portion is of substantially saddle-shaped configuration.

6. A joint prosthesis according to claim 1 wherein said first and second articulating surface portions are opposite to said first and second bone fixation surface portions.

7. A joint prosthesis according to claim 1 wherein said protuberant members terminate at outer peripheral edges of said first and second bone fixation surface portions.

8. An endoprosthesis comprising:
a first member having a hyperbolic paraboloid-shaped front surface portion, said first member including an opposite first rear concave bone fixation surface adapted to fit securely against a bone and at least two protuberant members;
a second member including a second front saddle-shaped surface portion complementary to said first front surface portion, said second member including an opposite second rear convex bone fixation surface and at least two protuberant members; and
a retaining member configured to releasably link together the first and second members and prevent movement therebetween, wherein the retaining member comprises at least a first and second post configured to releasably engage with the protuberant members of the first member and at least a third and fourth post configured to releasably engage with the protuberant members of the second member, the posts and protuberant members having parallel longitudinal axes to allow each post to be inserted into its respective protuberant member to link together the first and second implant members and, after implantation, allow each post to be slidably withdrawn from its respective protuberant member to allow the first and second implant members to articulate.

9. The endoprosthesis according to claim 8 wherein said hyperbolic paraboloid-shaped first front surface portion and said opposite second rear convex bone fixation surface are composed at least in part of a metal alloy.

10. The endoprosthesis according to claim 8 wherein said protuberant members are positioned on said first rear concave bone fixation surface and said second rear convex bone fixation surface, and wherein said protuberant members are porous members.

11. The endoprosthesis according to claim 10 wherein the protuberant members extend transversely to the first rear concave bone fixation surface and the second rear convex bone fixation surface.

12. The endoprosthesis according to claim 8 wherein said second front saddle-shaped surface portion is composed at least in part of a high density polyethylene and said second rear convex bone fixation surface is composed at least in part of a metal alloy.

13. The endoprosthesis according to claim 8 wherein said retaining member is configured to releasably link the first and second members together in an orientation suitable for implantation.

14. The endoprosthesis according to claim 8 wherein the retaining member includes an extension configured to be hammered upon during implantation of the endoprosthesis.

15. The endoprosthesis according to claim 8 wherein said posts are positioned on a first surface of the retaining member, and wherein the retaining member further comprises an extension configured to be hammered upon, the extension being positioned on a second surface of the retaining member, the second surface being opposite the first surface.

16. A humeral-radioulnar prosthesis comprising:
a hyperbolic paraboloid-shaped condyle member;
a complementary saddle-shaped radioulnar member;
concave bone-receiving means on a cranial surface of said condyle member and convex bone-receiving means on a caudal surface of said radioulnar member for fixation to proximal ends of a designated bone,
transverse extension members on said cranial surface of said condyle member and said caudal surface of said radioulnar member adapted to be embedded in said proximal ends; and
a retaining member configured to releasably link together the condyle and radioulnar members and prevent movement therebetween, the retaining member comprising at least a first and second post configured to engage with the condyle member and at least a third and fourth post configured to engage with the radioulnar member.

17. The prosthesis according to claim 16 wherein said transverse extension members include porous beads.

18. The prosthesis according to claim 16 wherein said condyle member includes a trochlear-shaped groove on a caudal surface of said condyle member.

19. The prosthesis according to claim 18 wherein said radioulnar member has a complementary trochlear-shaped ridge along the length of a cranial surface of said radioulnar member.

20. The prosthesis according to claim 19 wherein said trochlear-shaped ridge and said trochlea-shaped groove form articulating surfaces therebetween.

21. The prosthesis according to claim 16 wherein said transverse extension members are coextensive with outer peripheral edges of said condyle member and said radioulnar member.

22. The prosthesis according to claim 16, wherein said cranial surface of the condyle member and said caudal surface of the radioulnar member each include two or more porous protuberant members extending transversely to said cranial and caudal surfaces, and wherein the retaining member comprises at least a first and second post positioned to be at least partially inserted into the porous protuberant members on the cranial surface and at least a third and fourth post positioned to be at least partially inserted into the porous protuberant members on the caudal surface, the posts and protuberant members having parallel longitudinal axes to allow each post to be inserted into its respective protuberant member to link together the condyle and radioulnar members and, after implantation, allow each post to be slidably withdrawn from its respective protuberant member to allow the condyle and radioulnar members to articulate.

* * * * *